United States Patent [19]

Gimpelson

[11] Patent Number: 5,281,237
[45] Date of Patent: Jan. 25, 1994

[54] SURGICAL STITCHING DEVICE AND METHOD OF USE

[76] Inventor: Richard J. Gimpelson, 1028 Terrace Rock Cir., Ballwin, Mo. 63011

[21] Appl. No.: 951,867

[22] Filed: Sep. 25, 1992

[51] Int. Cl.$^5$ ............................................. A61B 17/00
[52] U.S. Cl. ................................... 606/144; 606/148; 606/139
[58] Field of Search .............. 606/146, 144, 147, 139, 606/148; 128/754

[56] References Cited

U.S. PATENT DOCUMENTS

| | | | |
|---|---|---|---|
| 2,496,111 | 1/1950 | Turkel | 128/754 |
| 2,738,790 | 3/1956 | Todt, Sr. et al. | 128/334 |
| 3,877,434 | 4/1975 | Ferguson et al. | 128/327 |
| 4,602,635 | 7/1986 | Mulhollan et al. | 128/334 |
| 4,712,545 | 12/1987 | Honkanen | 128/305 |
| 4,781,190 | 11/1988 | Lee | 128/334 |
| 4,784,139 | 11/1988 | Demos | 128/340 |
| 4,957,498 | 9/1990 | Caspari et al. | 606/146 |
| 4,976,269 | 12/1990 | Mehl | 128/754 |
| 5,015,250 | 5/1991 | Foster | 606/147 |
| 5,036,860 | 8/1991 | Leigh et al. | 128/754 |
| 5,059,201 | 10/1991 | Asnis | 606/144 |
| 5,090,419 | 2/1992 | Palestrant | 128/754 |

Primary Examiner—Stephen C. Pellegrino
Assistant Examiner—Gary Jackson
Attorney, Agent, or Firm—Grace J. Fishel

[57] ABSTRACT

A surgical stitching device allows a surgeon to place a "through and through" suture. The device includes a hollow needle with an inner needle slidingly disposed with the hollow needle. The inner needle has a groove which can be retracted within the hollow needle for grasping a suture. When the groove is filled with a suture and retracted in the hollow needle, the device can be used to make an incision through tissue and to deliver a length of suture to the bottom of the incision. The device can then be withdrawn or a second device with an empty groove used to make an incision through the tissue at a neighboring location. The device at the second incision is then used to regrasp the suture and to pull it through the tissue at the second incision. The ends of the suture at the first and second incisions are then tied in a knot around the tissue.

11 Claims, 2 Drawing Sheets

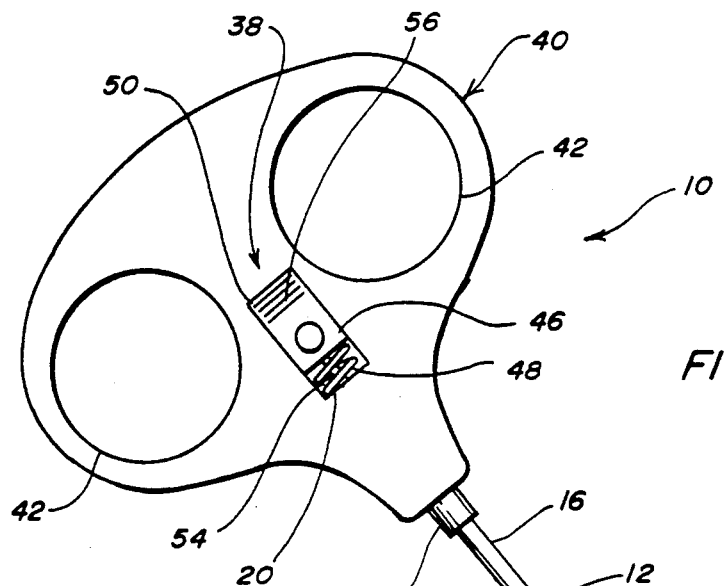
FIG. 1
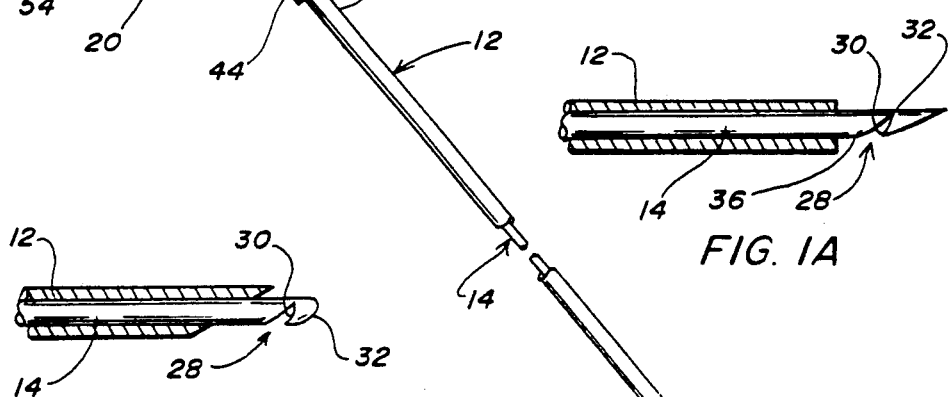
FIG. 1A
FIG. 1B
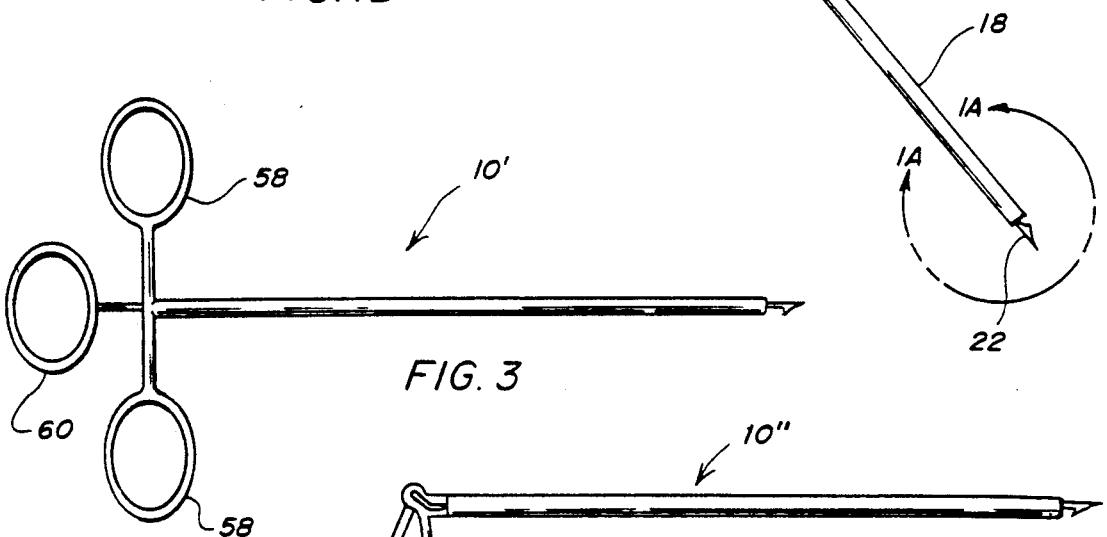
FIG. 3
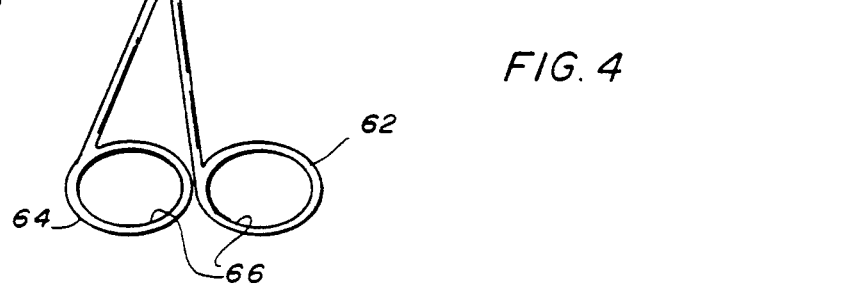
FIG. 4

SURGICAL STITCHING DEVICE AND METHOD OF USE

BACKGROUND OF THE INVENTION

1. Field of the Invention

The present invention relates to a surgical stitching device and to its use in closing laparoscopic incisions to prevent the development of hernias. The device may also be used for ligating an artery, ligament and so forth where suturing is otherwise difficult.

2. Brief Description of the Prior Art

Larger cannulas are needed to accommodate larger instruments in laparoscopy and to remove tissue specimens. The introduction of cannulas 10 mm or larger in diameter has led to an increased risk of incisional hernias. As reported by Kadar N., Reich H., Liu C. Y., Manko G. F. and Gimpelson R. J. in an article entitled "Incisional hernias following major laparoscopic gynecological procedures", the incidence of incisional hernia is greatly increased when a 10 mm or larger trocar is used at an extra-umbilical site. Under those circumstances, the authors believe that the underlying fascia should be closed and that even the peritoneum may require closure at a 12 mm trocar site.

Presently, large laparoscopic incisions are closed with curved or straight needles. Curved needles are often difficult to place with standard needle holders operating outside the abdomen. Whereas straight needles are inserted through fascia and peritoneum from outside to inside and then with laparoscopic graspers are manipulated from inside to outside again with much difficulty.

The surgical stitching device of the present invention allows a surgeon to place a "through and through" suture incorporating the fascia and peritoneum on each side of a laparoscopic incision with much less effort than is needed with present needles. The incision is then closed with an external knot.

SUMMARY OF THE INVENTION

In view of the above, it is an object of the present invention to provide a surgical stitching device which rapidly delivers a suture through fascia and peritoneum on one side of an incision and then regrasps the suture on the other side of the incision and pulls the suture through peritoneum and fascia allowing an external knot and closure of the incision. It is also an object to place an externally tied suture around an artery or ligament where suturing is otherwise difficult. Other objects and features of the invention will be in part apparent and in part pointed out hereinafter.

In accordance with the invention, a surgical stitching device has an elongated hollow needle and an inner needle slidably disposed within the hollow needle. The hollow needle and the inner needle each has a proximal end and a distal end. The inner needle has an angled groove opening proximally along one side adjacent its distal end. The inner needle also has a means at its proximal end for reciprocating the inner needle inside the hollow needle such that the groove is selectively covered and uncovered by the distal end of the hollow needle.

In use, the inner needle is retracted with a suture in the groove and the device inserted into a piece of tissue. The inner needle is reciprocated such that the groove is uncovered and the suture is deposited at the base of the incision. The device is then inserted into a neighboring location in the tissue with the groove empty. The inner needle is reciprocated such that the groove is uncovered and the device is manipulated such that the suture is caught in the groove. The suture is then pulled through the tissue at the second incision while it is held so that it does not pull out the first incision. The ends of the suture are then tied to form an external knot around the tissue.

The invention summarized above comprises the constructions and methods hereinafter described, the scope of the invention being indicated by the subjoined claims.

BRIEF DESCRIPTION OF THE DRAWINGS

In the accompanying drawings, in which several of various possible embodiments of the invention are illustrated, corresponding reference characters refer to corresponding parts throughout the several views of the drawings in which:

FIG. 1 is plan view of a surgical stitching device in accordance with the present invention;

FIG. 1A is a detail in section taken along line 1A—1A in FIG. 1;

FIG. 1B is a detail like FIG. 1A showing an alternate form;

FIG. 3 is a plan view of a second embodiment surgical stitching device; and,

FIG. 4 is a plan view of a third embodiment surgical stitching device.

DETAILED DESCRIPTION OF THE INVENTION

Figure 2A:
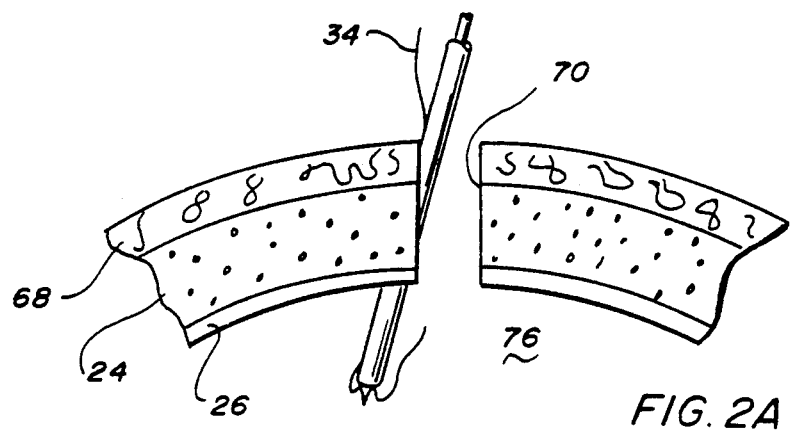
FIGS. 2A-2D are simplified (e.g., interleaved layers of subcutaneous fat and muscle are omitted) diagrammatic successive views in section showing closure of a laparoscopic incision with the surgical stitching device needle shown in FIG. 1.

Referring to the drawings more particularly by reference character, reference numeral 10 refers to a surgical stitching device in accordance with the present invention. In major part, device 10 includes an elongated hollow needle 12 with an inner needle 14 slidably disposed therein. Hollow needle 12 has a proximal end 16 and a distal end 18 and inner needle 14 has a proximal end 20 and a distal end 22.

Hollow needle 12 is straight and has a diameter such that it can be inserted through a patient's fascia 24 and peritoneum 26. For this purpose, hollow needle 12 preferably has a length in the range of about 5 to about 25 cm and a diameter of about 12 to about 20 gauge. Inner needle 14 is also straight and can be hollow or solid. It is preferably 1 to 2 gauges smaller than hollow needle 12 such that it is strong enough for its intended purpose yet can be easily reciprocated within hollow needle 12.

Referring now to FIG. 1A, an angled groove 28 is provided adjacent distal end 22 of inner needle 14. Angled groove 28 slopes proximally and tapers from an open proximal end 30 to a closed distal end 32 to permit easy lateral insertion of a suture 34 into the opening and to wedge the suture into tight frictional engagement with the groove. Along groove 28, the shaft of inner needle 14 is beveled 36 such that suture 34 is directed into groove 28.

In the embodiment illustrated in FIG. 1A, distal end 22 of inner needle 14 is sharpened such that it serves as a trocar for inserting device 10 while distal end 18 of hollow needle 12 is blunt. In this case, when inner needle is retracted as described below, groove 28 is covered by distal end 18 of hollow needle 12 while distal end 22 of inner needle 14 is exposed. Device 10 can be used to place a suture at the base of an incision (as more particularly described below) and retrieve it. In other instances, as shown in FIG. 1B, distal end 22 of inner needle 14 may be blunted to reduce the risk of intraabdonminal injury when device 10 is inserted into the peritoneal cavity and distal end 18 of hollow needle 12 is sharpened for use in punching through fascia 24 and peritoneum 26. Unless inner needle 14 is thinned at distal end 22 such that a length of suture 34 can be pulled inside hollow needle 12 along with inner needle 14, the modification shown in FIG. 1B cannot be used for placing suture 34 at the base of an incision.

A means 38 for reciprocating inner needle 14 is attached to proximal end 20 such that groove 28 is selectively covered and uncovered by hollow needle 12. As shown in FIG. 1, a handle 40 with a pair of finger holes 42 is attached by a collar 44 to hollow needle 12. Means 38 comprise a block 46 which reciprocates in an aperture 48 provided in handle 40 between proximal and distal limits 50, 52, respectively. A resilient biasing means 54 (illustrated as a coil spring or the like) is threaded around proximal end 20 of inner needle 14 and is sandwiched between block 46 and distal limit 32. Resilient biasing means 54 pushes block 46 towards proximal limit 50 in starting condition so that groove 28 is retracted within and covered by distal end 18 of hollow needle 12. Block 46 includes a thumb detent 56 for pushing block 46 towards distal limit 52, compressing resilient biasing means and uncovering groove 28 from distal end 18.

As shown in FIG. 3, means 38 for reciprocating inner needle 14 are not spring biased. In this example, handle 40 takes the form pair of finger loops 58 attached to hollow needle 12 and means 38 operates like a plunger and comprises a finger loop 60 attached to inner needle 14. In the embodiment shown in FIG. 4, handle 40 is a pistol grip 62 attached to hollow needle 12 and means 38 for reciprocating inner needle 14 is a trigger 64 which pivots on hollow needle 12. To facilitate gripping, finger holes 66 are provided in trigger 64 and pistol grip 62 of second and third embodiments, respectively.

Device 10 can be made of surgical grade stainless steel such that it can be autoclaved and reusable or parts of it can be made of plastic such that all or a portion of it can be disposed of after a single use. A disposable device 10 offers the benefits of being optimally sharp.

In use, device 10 functions as a needle, suture holder and grasper all in one easy to use instrument. It makes laparoscopic incision closure easy and minimizes the risk of incisional hernia formation. It can also be used to rapidly ligate an inferior epigastric artery that is injured on trocar insertion and, in general, can be used for placing an externally tied suture around a piece of tissue.

The following examples illustrate the invention.

EXAMPLE 1

Closure of a laparoscopic incision to prevent the development of hernias as shown in FIGS. 2A-2D.

With a scalpel blade, a nick is made through a layer of skin 68 on the patient's abdomen. The nick or small incision minimizes resistance to entry of the cannula and allows smooth, more controlled insertion. The cannula aperture 70 passes through fascia 24 and peritoneum 26.

After a laparoscopic procedure is completed, the cannula is withdrawn. If the cannula is 10 mm or larger in diameter, cannula aperture 70 should be closed to prevent the development of hernias. As shown in FIG. 2A, this can be accomplished with device 10 shown in FIG. 1. Inner needle 14 is extended under sliding pressure on block 46 from the surgeon's thumb. Suture 34 is grasped in groove 28 and when block 46 is released, resilient biasing means 54 retracts inner needle 14 trapping a piece of suture 34 at distal end 18 of hollow needle 12. Suture 34 is held against the shaft of hollow needle 12 while hollow needle 12 is inserted through fascia 24. Hollow needle 12 should also be passed through peritoneum 26 if the cannula was 12mm or larger or if the surgeon otherwise determines that it is desirable to stitch the peritoneum. Care is taken to avoid skin 68 and hollow needle 12 is inserted along one side of the nick made in the patient's skin for the reasons described below.

Figure 2B:
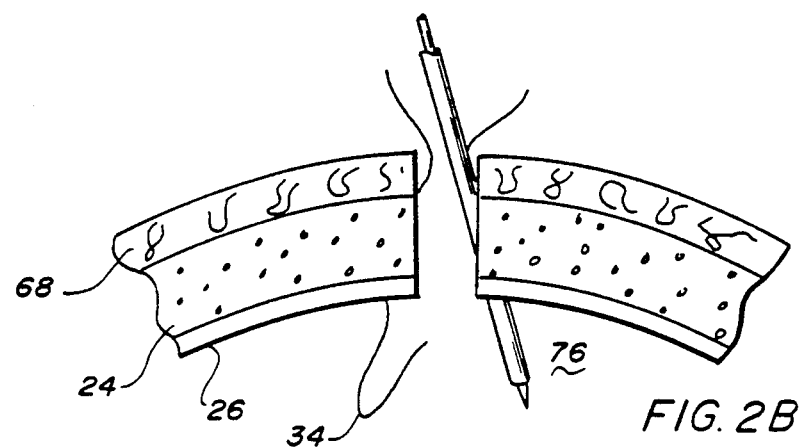

Referring to FIG. 2B, suture 34 is released at the base of the incision by extending inner needle 14 with means 38 for reciprocating such that suture 34 and groove 28 are uncovered at distal end 18 of hollow needle 12. Device 10 is removed from abdomen in the reverse direction that it is inserted. Device 10 is then inserted empty through fascia 24 (and peritoneum 26) on the opposite side of the nick at cannula aperture 70.

Figure 2C:
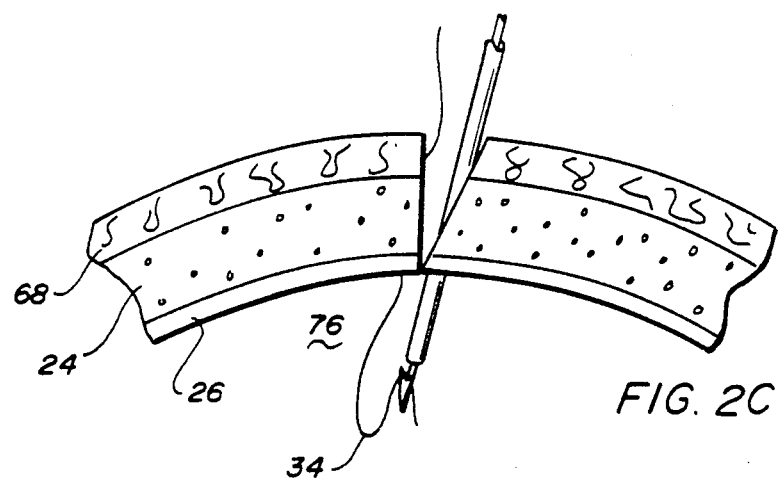

As shown in FIG. 2C, device 10 is used to regrasp suture 34. Inner needle 14 is extended such that groove 28 is uncovered at distal end 18 of hollow needle 12 where it is available for catching suture 34. Once device has regrasped suture 34 (This is best accomplished by an operator working in the same direction as the view on the laparoscopic TV monitor to avoid the confusion of working backward), that end of the suture on the opposite side of cannula aperture 70 is held while device 10 is withdrawn from the incision in the reverse direction that it is inserted. With both devices 10 withdrawn, the patient has a "through and through" suture incorporating fascia 24 (and peritoneum 26) on both sides of cannula aperture 70.

Figure 2D:
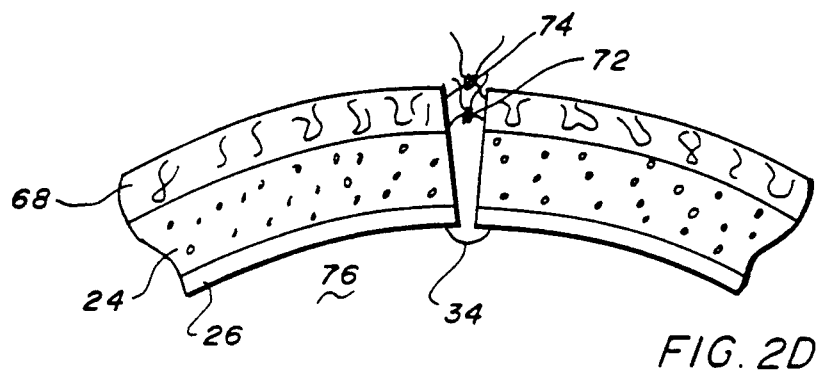

With reference to FIG. 2D, the ends of suture 34 are then easily tied into a knot 72 within the incision site and the laparoscopic incision closed. Additional sutures can be placed in the same manner. Skin 68 is then approximated over the deep stitch(es) at 74 to complete the closure.

In some instances, it may be preferred to leave device 10 with suture 34 in place after it is inserted (FIG. 2A) while a second device 10 is inserted empty through the opposite side of cannula aperture 70 (FIG. 2B). In this instance, suture 34 is released from first device 10 just before or after suture 34 is grasped by second device 10. First and second devices 10 are then withdrawn from the abdomen and suture 34 tied as described above.

Suture 34 may be held with graspers after it is released by the first device and while it is being regrasped by the second device.

EXAMPLE 2

Ligating an artery to control hemorrhage.

Occasionally, a trocar cuts an epiperitoneal artery in the abdominal wall (such as an inferior epigastric artery) when cannula aperture 70 is made and sometimes it is necessary to ligate the vessel to control hemorrhage.

Device 10 (or a pair of devices 10) is used as described in Example 1 to place a suture around the traumatized artery. Under endoscopic vision, suture 34 is inserted with device 10 through fascia 24 and peritoneum 26 into peritoneal cavity 76 on one side of the spurting vessel. Device 10 is withdrawn or a second device 10 is inserted empty on the opposite side of the vessel to reach under the vessel and regrasp suture 34 placed by the first device 10. Once suture 34 has been grasped by empty device 10, it (and first device 10 if not withdrawn previously) is drawn up through peritoneum 26 and fascia 24 to the surface where the ends of suture 34 are tied with sufficient pressure to ligate the spurting vessel. If there is time, skin 68 is nicked such that knot 72 is subcutaneous for cosmetic reasons but in an emergency, device 10 can be punched through skin 68 also.

EXAMPLE 3

Ligating a ligament for uterine suspension.

Under certain conditions that cause pelvic pain (e.g., endometriosis) and the uterus is in a retroverted position, it may benefit the patient to have the uterus suspended in an anterior manner.

Device 10 (or a pair of devices 10) might be used as described in Example 1 to place a suture or sutures through the round ligament. A lateral skin incision is made adjacent the round ligament and device 10 used to carry suture 34 through the fascia 24 and peritoneum 26 into the abdominal cavity 76 on one side of the incision. The same or a second device 10 is inserted empty through the other side of lateral skin incision on the opposite side of the ligament. Empty device 10 is then used to regrasp suture 34 which is released by first device 10. The first and second devices 10 are then withdrawn from the patient and the ends of the suture tied externally in the incision ligating the ligament. Additional sutures may be tied through the ligament as required and the skin incision closed above the deep stitches. The same is repeated on the opposite round ligament. With both round ligaments ligated against the peritoneum, the uterus will be suspended.

In view of the above, it will be seen that the several objects of the invention are achieved and other advantageous results attained. As various changes could be made in the above constructions and methods without departing from the scope of the invention, it is intended that all matter contained in the above description or shown in the accompanying drawings shall be interpreted as illustrative and not in a limiting sense.

What is claimed:

1. A surgical stitching device comprising an elongated hollow needle with a proximal end and a distal end, a handle attached to the proximal end of the hollow needle and an inner needle with a proximal end and a distal end slidably disposed within said hollow needle, said inner needle having a groove sized to catch and retain a conventional suture of the type used in surgery and angled proximally along one side adjacent the distal end and a means in the handle at the proximal end of the inner needle for reciprocating the inner needle inside the hollow needle such that the groove is slectively covered and uncovered by the distal end of the hollow needle whereby the stitching device can be used to carry a piece of suture caught in the groove through a piece of tissue as the stitching device is inserted into the tissue and then used to catch the suture and pull it through the tissue when the stitching device is inserted into the tissue at a neighboring location.

2. The stitching device of claim 1 wherein the groove tapers from an open proximal end to a closed distal end and wherein the inner needle is beveled along the groove for directing the suture into the groove.

3. The stitching device of claim 1 wherein the distal end of the inner needle is sharpened and is exposed when the groove is covered by the distal end of the hollow needle whereby the distal end of the inner needle serves as a trocar during insertion of the stitching device.

4. The stitching device of claim 1 wherein the distal end of the inner needle is blunted and is covered when the groove is covered by the distal end of the hollow needle and wherein the distal end of the hollow needle is sharpened whereby the distal end of the hollow needle serves as a trocar during insertion of the stitching device.

5. A surgical stitching device comprising an elongated hollow needle with a proximal end and a distal end, a handle attached to the proximal end of the hollow needle and an inner needle with a proximal end and a distal end slidably disposed within said hollow needle, said inner needle having a groove sized to catch and retain a conventional suture of the type used in surgery and angled proximally along one side adjacent the distal end and a means in the handle at the proximal end of the inner needle for reciprocating the inner needle inside the hollow needle such that the groove is selectively covered and uncovered by the distal end of the hollow needle, said groove tapering from an open proximal end to a closed end and the inner needle being beveled along the groove for directing a suture into the groove, said means for reciprocating the inner needle being resiliently biased between a proximal limit wherein the groove is covered by the distal end of the hollow needle and a distal limit wherein the groove is uncovered, whereby the stitching device can be used to carry the suture caught in the groove through a piece of tissue and then used to catch the suture and pull it through the tissue when the stitching device is inserted into the tissue at a neighboring location.

6. The stitching device of claim 5 wherein said handle has an aperture and finger holes, said means for reciprocating the inner needle comprising a block attached to the inner needle and slidingly received in the aperture and said upper and lower limits comprising sides of the aperture.

7. The stitching device of claim 6 wherein the resilient biasing means are sandwiched between the block and the distal limit such that the inner needle is retracted in starting position.

8. A method of suturing a piece of tissue comprising the steps of:
   (a) providing one or more surgical stitching devices comprising an elongated hollow needle with a proximal end and a distal end and an inner needle with a proximal end and a distal end slidably disposed within said hollow needle, said inner needle having a groove angled proximally along one side adjacent the distal end and a means at the proximal end for reciprocating the inner needle inside the hollow needle such that the groove is selectively covered and uncovered by the distal end of the hollow needle;
   (b) making a first incision in the tissue with one of the surgical stitching devices after reciprocating the inner needle with said means for reciprocating such that the groove is uncovered at the distal end of the hollow needle, catching a piece of suture in the groove and then reciprocating the inner needle with said means for reciprocating such that the groove is covered at the distal end of the hollow needle;

(c) making a second incision at a neighboring location in the tissue with one of the surgical stitching devices;

(d) reciprocating the inner needle at the first incision with said means for reciprocating such that the suture and groove are uncovered at the distal end of the hollow needle and withdrawing the stitching device leaving the suture in the tissue;

(e) reciprocating the inner needle at the second incision with said means for reciprocating such that the groove is uncovered at the distal end of the hollow needle, manipulating the tissue such that the suture released at the first incision is caught in the groove of the stitching device at the second incision and pulling the suture through the tissue at the second incision while securing the suture such that it does not pull out of the first incision; and, (f) tying the ends of the suture at the first and second incisions to form a knot around the tissue.

9. A method for closing a laparoscopic incision comprising the steps of:

(a) providing one or more surgical stitching devices comprising an elongated hollow needle with a proximal end and a distal end and an inner needle with a proximal end and a distal end slidably disposed within said hollow needle, said inner needle having a groove angled proximally along one side adjacent the distal end and a means at the proximal end for reciprocating the inner needle inside the hollow needle such that the groove is selectively covered and uncovered by the distal end of the hollow needle;

(b) making a first incision with one of the surgical stitching devices after reciprocating the inner needle with said means for reciprocating such that the groove is uncovered at the distal end of the hollow needle, catching a piece of suture in the groove and then reciprocating the inner needle with said means for reciprocating such that the groove is covered at the distal end of the hollow needle, said first incision being generally vertical and through the fascia on one side of the laparoscopic incision;

(c) making a second generally vertical incision with one of the surgical stitching devices through the fascia at a location generally across the laparoscopic incision from the first incision;

(d) reciprocating the inner needle at the first incision with said means for reciprocating such that the suture and groove are uncovered at the distal end of the hollow needle and withdrawing the stitching device leaving the suture at the bottom of the first incision;

(e) reciprocating the inner needle at the second incision with said means for reciprocating such that the groove is uncovered at the distal end of the hollow needle, manipulating the tissue such that the suture that is released at the first incision is caught in the groove of the stitching device at the second incision and pulling the suture through the tissue at the second incision while securing the suture such that it does not pull out of the first incision; and, (f) tying the ends of the suture at the first and second incisions to form a knot closing the laparoscopic incision.

10. The method of claim 9 wherein the first and second incisions are made through the fascia and peritoneum on generally opposite sides of the laparoscopic incision.

11. The method of claim 10 wherein the skin around the laparoscopic incision is closed above the knotted suture through the fascia and peritoneum.

* * * * *